United States Patent
Fairhurst et al.

[19]

[11] Patent Number: 6,166,040
[45] Date of Patent: Dec. 26, 2000

[54] INDOLE COMPOUNDS

[75] Inventors: John Fairhurst, Winchester; Peter Thaddeus Gallagher, Yateley; Martin Victor Miles, Hampton; William Martin Owton, Lightwater; Colin William Smith, Bracknell, all of United Kingdom

[73] Assignee: Eli Lilly and Company Limited, Basingstoke, United Kingdom

[21] Appl. No.: 09/309,420

[22] Filed: May 11, 1999

[30] Foreign Application Priority Data

May 13, 1998 [GB] United Kingdom .................. 9810886

[51] Int. Cl.⁷ .................. A61K 31/40; A61K 31/435; C07D 401/00; C07D 209/36
[52] U.S. Cl. .................. 514/337; 514/337; 514/212; 514/414; 540/524; 546/201; 548/484
[58] Field of Search ............... 540/524; 546/201, 546/277.7; 548/484; 514/212, 414, 320, 337

[56] References Cited

U.S. PATENT DOCUMENTS

| | | | |
|---|---|---|---|
| 3,981,881 | 9/1976 | Wade et al. | 260/295 |
| 5,773,448 | 6/1998 | Gallagher et al. | 514/323 |

FOREIGN PATENT DOCUMENTS

| | | | |
|---|---|---|---|
| 0708102 A1 | 4/1996 | European Pat. Off. | C07D 401/14 |
| 0780388 | 12/1996 | European Pat. Off. | |
| WO 93/12085 | 6/1993 | WIPO | C07D 209/34 |
| WO 96/23784 | 8/1996 | WIPO | C07D 401/14 |

OTHER PUBLICATIONS

Patent Abstracts of Japan, 016:071, 03264581, Feb. 21, 1992.

Primary Examiner—John Kight
Assistant Examiner—Binta Robinson
Attorney, Agent, or Firm—Manisha A. Desai; Suzanne M. Harvey

[57] ABSTRACT

Pharmaceutical compounds of the formula:

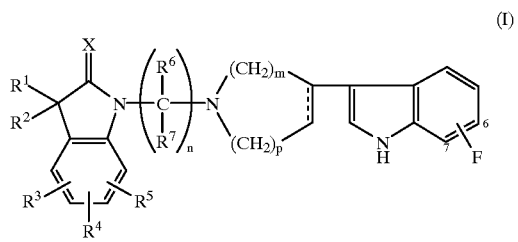

(I)

in which n is 1 to 6, m is 1 or 2 and p is 1 or 2, $R^1$ and $R^2$ are each hydrogen, $C_{1-4}$ alkyl, $C_{1-4}$ alkoxy, HO—$C_{1-4}$ alkyl, $C_{1-4}$ alkoxy-$C_{1-4}$ alkyl, $C_{1-4}$ alkylthio, halo, optionally substituted phenyl, optionally substituted phenyl-$C_{1-4}$ alkyl, or $R^1$ and $R^2$ together with the carbon atom to which they are attached form a $C_{3-6}$ cycloalkyl group, >C=O, C=NOR' where R' is hydrogen or $C_{1-4}$ alkyl, $R^3$, $R^4$ and $R^5$ are each hydrogen, halo, nitro, $C_{1-4}$ alkyl, $C_{1-4}$ alkoxy, $C_{1-4}$ alkyl-CO—, where m is 0, 1 or 2, R'R"N—$SO_2$—, —COOR', —CONR'R", —NR'R", —N(OR')COOR", —COR', —NHSO$_2$R', where R' and R' are each hydrogen or $C_{1-4}$ alkyl, $R^6$ and $R^7$ are each hydrogen or $C_{1-4}$ alkyl, X is oxygen or sulphur, the dotted line represents an optional double bond, and the fluorine atom is attached at the 6- or 7-position; and salts thereof.

8 Claims, No Drawings

INDOLE COMPOUNDS

This invention relates to pharmaceutical compounds, their preparation and use.

Compounds of the indole-2-one type have been described in the literature as having potential use as analgesics or for treating cognitive disorders or as cholinesterase inhibitors as, for example, in J. Med. Chem. 1991, 34, 827–841, WO 93/12085 and CA 119: 225964t.

EP-A 0 780 388 discloses certain indole-2-one compounds with central nervous system properties.

The compounds of the invention are of the following formula:

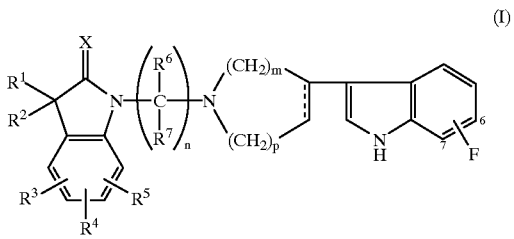

(I)

in which n is 1 to 6, m is 1 or 2 and p is 1 or 2, $R^1$ and $R^2$ are each hydrogen, $C_{1-4}$ alkyl, $C_{1-4}$ alkoxy, $HO-C_{1-4}$ alkyl, $C_{1-4}$ alkoxy-$C_{1-4}$ alkyl, $C_{1-4}$ alkylthio, halo, optionally substituted phenyl, optionally substituted phenyl-$C_{1-4}$ alkyl, or $R^1$ and $R^2$ together with the carbon atom to which they are attached form a $C_{3-6}$ cycloalkyl group, >C=O, >C=NOR' where R' is hydrogen or $C_{1-4}$ alkyl, $R^3$, $R^4$ and $R^5$ are each hydrogen, halo, nitro, $C_{1-4}$ alkyl, $C_{1-4}$ alkoxy, $C_{1-4}$ alkyl-CO—, where m is 0, 1 or 2, R'R"N—$SO_2$—, —COOR', —CONR'R", —NR'R", —N(OR')COOR", —COR', —$NHSO_2R'$, where R' and R" are each hydrogen or $C_{1-4}$ alkyl, $R^6$ and $R^7$ are each hydrogen or $C_{1-4}$ alkyl, X is oxygen or sulphur, the dotted line represents an optional double bond, and the fluorine atom is attached at the 6- or 7-position; and salts thereof.

The compounds of the invention and their pharmaceutically acceptable salts are indicated for use in the treatment of disorders of the central nervous system. They are active in tests that indicate serotonergic modulation.

In the above formula (I), a $C_{1-4}$ alkyl group includes methyl, ethyl, propyl, isopropyl, butyl and tert. butyl, and is preferably methyl or ethyl. A $C_{1-4}$ alkoxy group is one such alkyl group linked to a ring via an oxygen atom, and a halo atom is preferably chlorine, bromine or fluorine, and especially chlorine or fluorine. A substituted phenyl group is phenyl substituted with one or more, for example one to three, substituents selected from, for example, $C_{1-4}$ alkyl, especially methyl, $C_{1-4}$ alkoxy, especially methoxy and ethoxy, hydroxy, nitro, cyano, halo, especially chloro or fluoro, trihalomethyl, especially trifluoromethyl, carboxy and $C_{1-4}$ alkoxy-carbonyl. An optionally substituted phenyl-$C_{1-4}$ alkyl group is an optionally substituted phenyl attached through a $C_{1-4}$ alkyl group, and is preferably optionally substituted phenyl-$(CH_2)_x$— where x is 1 or 2, and most preferably optionally substituted benzyl.

It will be appreciated that when n is more than one, the recurring unit is not necessarily the same.

Preferred compounds are those which exhibit one or more of the following features:

(i) the fluorine substituent is in the 6-position (ii) x is oxygen (iii) the dotted line represents a double bond (iv) m is 2 and p is 1

(v) $R^1$ and $R^2$ are each hydrogen, $C_{1-4}$ alkyl or $C_{1-4}$ alkylthio (vi) $R^1$ and $R^2$ are both $C_{1-4}$ alkyl or benzyl (vii) n is 2

(viii) $R^6$ and $R^7$ are hydrogen (ix) $R^3$, $R^4$ and $R^5$ are each hydrogen.

As indicated above, it is, of course, possible to prepare salts of the compound of the invention and such salts are included in the invention. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to the pharmaceutically acceptable salts, other salts are included in the invention. They may serve as intermediates in the purification of compounds or in the preparation of other, for example pharmaceutically acceptable, acid addition salts, or are useful for identification, characterisation or purification.

Some of the compounds of the invention contain one or more asymmetric carbon atoms which gives rise to isomers. These compounds are normally prepared as racemic mixtures and can conveniently be used as such, but individual isomers can be isolated by conventional techniques, if so desired. Such racemic mixtures and individual optical isomers form part of the present invention. It is preferred to use an enantiomerically pure form.

A preferred group of compounds according to the invention is of formula:

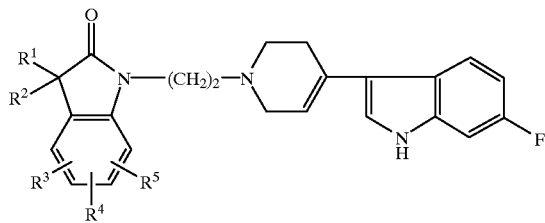

in which $R^1$ and $R^2$ are each hydrogen or $C_{1-4}$ alkyl, and $R^3$, $R^4$ and $R^5$ are each hydrogen;

and salts thereof.

The invention also includes a process for producing a compound of formula (I) above, which comprises reacting a compound of the formula:

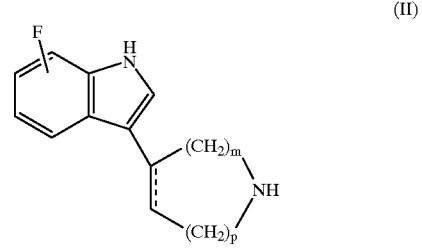

(II)

with a compound of the formula:

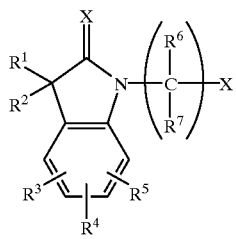

(III)

where the substituents have the values given above, and X is a leaving group such as, for example, a halo atom, or a mesylate or tosylate. The coupling can also be effected by reacting the compound of formula (II) with an aldehyde equivalent of the compound of formula (III). Such aldehydes can be prepared from the appropriate terminal alkene by oxidation followed by reductive amination using sodium cyanoborohydride with the compound of formula (II).

The reaction is preferably carried out in a polar solvent such as, for example, acetonitrile or water, at a temperature of from 50° C. to 150° C., and in the presence of sodium iodide and a base such as, for example, sodium carbonate.

The intermediate compounds of formula (II) and formula (III) are known in the art. Compounds of formula (III) can be prepared by reacting the appropriate alkane derivative of formula:

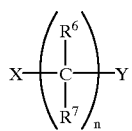

(IV)

where X is a leaving group and Y is halo, preferably bromo, with a compound of formula:

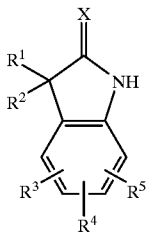

(V)

As mentioned above, the compounds of the invention and their pharmaceutically acceptable salts have useful central nervous system activity. The compounds are active at the serotonin, 5-HT2A, receptor. Their binding activity has been demonstrated in a test described by Leysen, J. E. et al., Molecular Pharmacology Vol. 21, 1981, pages 301–314, in which the affinity of the compound for the 2A receptor is measured by its ability to displace the ligand [$^3$H] ketanserine. The compounds are also an active serotonin reuptake inhibitor as measured by its displacement of [$^3$H] paroxetine at the reuptake site, Neuropharmacology Vol. 32 No. 8, 1993, pages 737–743.

Because of their selective affinity for 5-HT receptors, the compounds of the present invention are indicated for use in treating a variety of conditions such as depression, obesity, bulimia, alcoholism, pain, hypertension, ageing, memory loss, sexual dysfunction, anxiety, schizophrenia, gastrointestinal disorders, headache, cardiovascular disorders, smoking cessation, drug addiction, emesis, Alzheimer's and sleep disorders.

The compounds of the invention are effective over a wide dosage range, the actual dose administered being dependent on such factors as the particular compound being used, the condition being treated and the type and size of mammal being treated. However, the dosage required will normally fall within the range of 0.01 to 20 mg/kg per day, for example in the treatment of adult humans, dosages of from 0.5 to 100 mg per day may be used.

The compounds of the invention will normally be administered orally or by injection and, for this purpose, the compounds will usually be utilised in the form of a pharmaceutical composition. Such compositions are prepared in a manner well known in the pharmaceutical art and comprise at least one active compound.

Accordingly the invention includes a pharmaceutical composition comprising as active ingredient a compound of formula (I) or a pharmaceutically acceptable salt or ester thereof, associated with a pharmaceutically acceptable excipient. In making the compositions of the invention, the active ingredient will usually be mixed with a carrier, or diluted by a carrier, or enclosed within a carrier which may be in the form of a capsule, sachet, paper or other container. The excipient may be a solid, semi-solid or liquid material which acts as a vehicle, excipient or medium for the active ingredient. Some examples of suitable excipients are lactose, dextrose, sucrose, sorbitol, mannitol, starches, gum acacia, calcium phosphate, alginates, tragacanth, gelatin syrup, methyl cellulose, methyl- and propyl-hydroxybenzoate, talc, magnesium stearate or oil. The compositions of the invention may, if desired, be formulated so as to provide quick, sustained or delayed release of the active ingredient after administration to the patient.

Depending on the route of administration, the foregoing compositions may be formulated as tablets, capsules or suspensions for oral use and injection solutions or suspensions for parenteral use or as suppositories. Preferably the compositions are formulated in a dosage unit form, each dosage containing from 0.5 to 100 mg, more usually 1 to 100 mg, of the active ingredient.

The following Preparations and Examples illustrate methods of making compounds of the invention.

PREPARATIONS (1) N-Acetyl-1,3-dihydro-2H-indol-2-one 1,3-Dihydro-2H-indol-2-one (35.6 g, 0.268 mol) suspended in acetic anhydride (30 mls) and mixture refluxed for 20 hours. Filtered and washed with diethyl ether (50 mls) dried in vacuo at 80 deg C. to give a solid.

3-Spiro-1'-cyclopropyl-1,3-dihydro-2H-indol-2-one

N-Acetyl-1,3-dihydro-2H-indol-2-one (15.0 g, 85.7 mmols) dissolved in dimethylformamide (180 mls) and added to suspension of sodium hydride (60% in oil dispersion, 7.2 g, 4.32 g, 0.18 mol) in dimethylformamide (30 mls). After 30 minutes 1,2-dibromoethane (17.71 g, 94.27 mmols) was added and the mixture stirred at ambient temperature for 20 hours. More sodium hydride (1.4 g, 0.84 g, 14 mmol) was added followed by 1,2-dibromoethane (4 g, 21.96 mmol) and stirred for 1 h at ambient temperature. The solvent was removed in vacuo and the residue treated with water (100 mls) added extracted with ethyl acetate (2×150 mls), separated and dried (MgSO$_4$), filtered and concentrated in vacuo to give an oil which was purified by column chromatography on silica eluting with ethyl acetate/hexane to give 3-spiro-1'-cyclopropyl-1,3-dihydro-2H-indol-2-one as an oil.

$^1$H NMR (CDCl$_3$) d1.54 (2H m), 1.78 (2H m), 6.82 (1H d), 7.02 (2H m), 7.22 (1H m), 9.0 (1H broad)

(2) Cyclobutylphenylhydrazide

Phenylhydrazine (9.21 g, 85.2 mmols) was added to an ice bath cooled mixture of cyclobutane carbonyl chloride (10.1 g, 85.2 mmols) and triethylamine (8.62 g, 85.2 mmols) dissolved in dichloromethane (100 mls) allowed to warm to ambient temperature and stirred for 48 h. The organic layer was washed with water, separated. dried (MgSO$_4$), filtered and concentrated in vacuo. The resultant solid was washed with diethyl ether (10 mls) and dried under suction to give a solid.

3-Spiro-1'-cyclobutyl-1,3-dihydro-2H-indol-2-one

Cyclobutylphenylhydrazide (7.14 g, 37.6 mmols) combined with calcium hydride (2.37 g) and heated to 240 deg C. for 30 mins., cooled and methanol(40 mls) and water (10 mls) added followed by hydrochloric acid (d=1.16 g/ml, 30 mls) the resultant mixture heated under reflux for 1 h., then basified with 5M sodium hydroxide to pH11 and the mixture extracted with diethyl ether. The ether layer was separated and dried (MgSO$_4$), filtered and concentrated in vacuo to give an oil which was chromatographed on silica eluting with ethyl acetate/hexane silica to give 3-spiro-1'-cyclobutyl-1,3-dihydro-2H-indol-2-one as an oil.

(3) 3-Spiro-1'-cyclopentyl-1,3-dihydro-2H-indol-2-one

N-acetyl oxindole (5.0 g,28.6 mmols) was dissolved in tetrahydrofuran (100 mls) under nitrogen, cooled to −78C and 2.0M lithium diisopropylamide in THF (15.45 ml, 30.9 mmol) added and left to stir for 30 mins. 1,4-dibromobutane (6.48 g, 30 mmols) added and mixture left for 1 hour at −78C. More lithium diisopropylamide in THF (15.45 ml, 30.9 mmol) added and the mixture left to warm to ambient temperature. The solvent was removed in vacuo and water (100 mls) added, the aqueous extracted with ethyl acetate (2×150 ml). The aqueous layer was separated, the organic layer dried (MgSO$_4$), filtered and concentrated in vacuo. The residue was purified by column chromatography on silica with ethyl acetate/hexane to give 3-spiro-1'-cyclopentyl-1, 3-dihydro-2H-indol-2-one as an oil.

(4) Cyclohex-3,4-enylphenylhydrazide

A mixture of cyclohex-3-ene-1-carboxylic acid (15.23 g, 0.120 mols), and phenylhydrazine (13.16 g 0.122 mols) dissolved in toluene (100 mls) and heated under reflux for 18 h with water separation using a Dean Stark apparatus. The toluene evaporated in vacuo and the residue recrystallised from diethyl ether to give a solid.

3-Spiro-1'-cyclohexyl-1,3-dihydro-2H-indol-2-one

To a −78C solution of 1,3-dihydro-2H-indol-2-one (10 g, 75.1 mmols) dissolved in tetrahydrofuran (200 mls) was added lithium bis(trimethylsilylamide) (1.0M in THF, 375 mls, 0.375 mol) was added keeping the temperature below −40C. The mixture was allowed to stir for 150 minutes at −40C cooled to −78C and 1,5-dibromopentane (86.35 g 0.375 mols) addded. The reaction mixture was allowed to warm to ambient temperature and stirred for 3 hours then heated under reflux for 7 hours, concentrated in vacuo, dissolved in ethyl acetate (200 mls) and washed with saturated aqueous ammonium chloride (100 mls), dried (MgSO$_4$), filtered and concentrated in vacuo. The resultant solid was purified by chromatography (silica/ethyl acetate/ hexane) to give 3-spiro-1'-cyclohexyl-1,3-dihydro-2H-indol-2-one as a solid.

(5) Methyl 2-nitrophenylacetate

A mixture of 2-nitrophenylacetic acid (300 g, 1.66 mol) and sulfuric acid (d=1.84 g/ml, 6 ml) in methanol (6l) was heated under reflux for 21 h. The solvent was removed in vacuo and the residue dissolved in dichloromethane (2l). The dichloromethane solution was then washed with saturated aqueous sodium carbonate solution (600 ml), brine (500 ml), dried (MgSO$_4$), filtered and then evaporated in vacuo.

Methyl 2-methyl-2-(2-nitrophenyl)propionate

Hexane (100 ml) was added to sodium hydride (60%, 180 g, 4.5 mol) and stirred under nitrogen for 5 minutes and then allowed to settle. The hexane was removed by decantation and replaced with dry dimethylformamide (3l). More sodium hydride (unwashed 14 g, 0.35 mol) was then added and the reaction mixture was cooled to 5C and treated with methyl 2-nitrophenylacetate (323 g 1.66 mol) in dry dimethylformamide (1500 ml) during 27mins whilst the internal temperature was kept below 5C. The mixture was then allowed to stir for 2 h allowing the temperature to rise to ambient. The purple reaction mixture was then cooled to 0C and a solution of iodomethane (367 ml, 5.8 mol) in dry dimethylformamide was added dropwise during 38 mins at 0–5C and maintained at this temperature for 45 mins then allowed to warm to ambient temperature and stirred for 22 h. The reaction mixture was then poured onto ice (5 kg) diluted with water (8000 ml) stirred for 10 mins and then extracted with diethyl ether (3×1500 ml), the organic extracts combined filtered through celite, dried (MgSO$_4$), filtered and evaporated in vacuo to give an oil which was used without further purification.

3,3-Dimethyl-1,3-dihydro-2H-indol-2-one

To a well stirred mixture of iron powder (476 g, 8.52 mol) in acetic acid (3000 ml) at 92C under nitrogen was added dropwise during 40 mins a solution of methyl 2-methyl-2-(2-nitrophenyl)propionate (395 g, 1.77 mol) in acetic acid (500 ml). The resultant exothermic reaction was maintained at 100C for 15 mins cooled to 30C, filtered and the filtered iron washed with acetic acid, combined with the reaction mixture and evaporated in vacuo to give a residue which was dissolved in ethyl acetate and then washed with hydrochloric acid (1000 ml), brine (1000 ml), dried (MgSO$_4$) filtered and evaporated in vacuo to give a crystalline solid.

(6) 3-Methyl-3-methylthio-1,3-dihydro-2H-indol-2-one 1,3-Dihydroindol-2(3H)-one (3.3 g,25 mmol) and tetramethylethylenediamine (6.4 g, 55 mmol) was dissolved in freshly distilled tetrahydrofuran under nitrogen and cooled to −75° C. in an acetone/dry ice bath. n-Butyllithium (2.5M, 22 ml, 55 mmol) was added and the mixture was stirred at −75° C. for 30 minutes. Iodomethane (3.57 g, 25 mmol) was added and the mixture was allowed to warm to −20° C., the mixture was recooled to −75° C. then dimethyl disulfide (2.35 g, 25 mmol) was added and the mixture was allowed to warm to room temperature. Water (5 ml) was added and the mixture was concentrated under reduced pressure to a yellow oil. Column chromatography on silica gel (eluent ethyl acetate/hexane) gave 3-methyl-3-methylthio-1,3-dihydro-2H-indol-2-one as a yellow oil which solidified on standing.

$^1$H NMR (CDCl$_3$) d 1.61(3H s), 1.91(3H s), 6.96(1H d), 7.04(1H t), 7.12(2H m), 8.05 (1h broad).

(7) 5-Bromo-3,3-dimethyl-1,3-dihydro-2H-indol-2-one 3,3-dimethyl-1,3-dihydro-2H-indol-2-one (1.12 g, 6.95 mmol) was dissolved in chloroform and stirred at room temperature under nitrogen. Bromine (1.12 g) was added and the mixture was heated under reflux until HBr evolution ceased and the bromine colour was discharged from the solution. The solution was washed with sodium metabisulphite solution and sodium hydrogen carbonate solution, dried (MgSO$_4$), filtered and concentrated to dry under reduced pressure to give 5-bromo-3,3-dimethyl-1,3-dihydro-2H-indol-2-one as a yellow solid.

$^1$H NMR (CDCl$_3$) d1.39 (6H s), 6.8 (1H d), 7.3 (2H m), 7.9 (1H broad)

(8) 5,6-Difluoro-1,3-dihydro-2H-indol-2-one 3,4-Difluoroacetonitrile (5 g, 32.7 mmol) was added dropwise to 90% fuming nitric acid (25 ml) stirred and cooled in an ice/water bath. After 15 hours' stirring the mixture was poured into water, neutralised with sodium bicarbonate and extracted into dichloromethane. The organic phase was dried (MgSO$_4$), filtered and concentrated under reduced pressure. The resulting oil was dissolved in boron trifluoride acetic acid complex (30 ml), water (1 ml) was added and the mixture was heated under reflux for three hours. The mixture was poured into water, the pH was adjusted to pH4 and the mixture was extracted with ethyl acetate. The organic phase was dried (MgSO$_4$), filtered and concentrated under reduced pressure. The resulting oily solid was dissolved in acetic acid, iron powder was added and the mixture was heated under reflux for 1 hour. The mixture was filtered through Celite and concentrated under reduced pressure to a dark oil. Column chromatography on silica gel (eluent chloroform/methanol) gave 5,6-difluoro-1,3-dihydro-2H-indol-2-one as an orange solid.

$^1$H NMR (CDCl$_3$) d 3.48(2H s), 6.7(1H dd), 7.05(1H dd), 8.65(1H broad)

(9) 3,3,4-Trimethyl-1,3-dihydro-2H-indol-2-one and 3,3,6-Trimethyl-1,3-dihydro-2H-indol-2-one Prepared from N-isobutyl-3-methylphenylhydrazide by the method of Endler and Becker; Organic Syntheses Coll. vol. 4 page 657 and separated by preparative HPLC.

Melting point 3,3,4-Trimethyl-1,3-dihydro-2H-indol-2-one –133° C.

Melting point—3,3,6-Trimethyl-1,3-Dihydro-2H-indol-2-one –178° C.

(10) 3,3-Dimethyl-1-(2-hydroxy-1-ethyl)-1,3-dihydro-2H-indol-2-one 3,3-Dimethyl-1,3-dihydro-2H-indol-2-one (6.3 g, 40 mmol) was dissolved in dry dimethylformamide under nitrogen at room temperature. Sodium hydride (60% dispersion in mineral oil, 1.8 g, 45 mmol) was added and the mixture was stirred until gas evolution ceased. 2-(2-Chloroethoxy) tetrahydro-2H-pyran (7.5 g, 42 mmol) and sodium iodide (0.6 g, 4 mmol) was added and the mixture was warmed to 75° C. for 15 hours. Water was added and the mixture was concentrated under reduced pressure. The residue was taken up in ethyl acetate, washed (×3) with water, dried (MgSO$_4$), filtered and concentrated under reduced pressure. The resulting oil was taken up in methanol, para toluenesulphonic acid (0.75 g, 4 mmol) was added and the mixture was stirred at room temperature for 12 hours. The mixture was concentrated under reduced pressure, taken up in ethyl acetate, washed (×3) with aqueous sodium hydrogen carbonate solution dried (MgSO$_4$), filtered and concentrated under reduced pressure. The resulting oil was purified by chromatography on silica gel, eluent hexane/ethyl acetate, to give 3,3-dimethyl-1-(2-hydroxy-1-ethyl)-1,3-dihydro-2H-indol-2-one which was characterised by $^1$H nmr and MS.

$^1$H NMR (CDCl$_3$) d 1.4(6H s), 3.05 (1H broad), 3.95(4H s), 6.96(1H d), 7.04(1H t), 7.12(2H m).

MS shows 206 (MH$^+$) base peak.

(11) 1-(2-Hydroxy-1-ethyl)-3-methyl-3-methylthio-1,3-dihydro-2H-indol-2-one

Prepared from 3-methyl-3-methylthioindol-2(3H)-one and 2-(2-chloroethoxy)tetrahydro-2H-pyran as described for 3,3-dimethyl-1-(2-hydroxy-1-ethyl)-1,3-dihydro-2H-indol-2-one.

MS shows 238 (MH$^+$) base peak.

(12) 3-Ethyl-1-(2-hydroxy-1-ethyl)-3-methyl-1,3-dihydro-2H-indol-2-one

Prepared from 3-ethyl-3-methylindol-2(3H)-one (prepared by the method of Endler and Becker; Organic Syntheses Coll. vol. 4 page 657) and 2-(2-chloroethoxy) tetrahydro-2H-pyran as described in above.

MS shows 220 (MH$^+$) base peak.

(13) 5-Bromo-3,3-dimethyl-1-(2-hydroxy-1-ethyl)-1,3-dihydro-2H-indol-2-one

Prepared from 5-bromo-3,3-dimethyl-1,3-dihydro-2H-indol-2-one and 2-(2-chloroethoxy)tetrahydro-2H-pyran as described above.

$^1$H NMR (CDCl$_3$) d1.39 (6H s), 3.05 (1H broad), 3.95(4H s), 6.8 (1H d), 7.3 (2H m),

(14) 1-(2-Hydroxy-1-ethyl)-3,3,5-trimethyl-1,3-dihydro-2H-indol-2-one

Prepared from 3,3,5-trimethyl-1,3-dihydro-2H-indol-2-one (prepared by the method of Endler and Becker; Organic Syntheses Coll. vol. 4 page 657) and 2-(2-chloroethoxy) tetrahydro-2H-pyran as described above.

MS shows 220 (MH$^+$) base peak and 237 (M+NH$_4$)

(15) 5-Chloro-3,3,dimethyl-1-(2-hydroxy-1-ethyl)-1,3-dihydro-2H-indol-2-one

Prepared from 5-chloro-3,3,dimethyl-1,3-dihydro-2H-indol-2-one (prepared by the method of Endler and Becker; Organic Syntheses Coll. vol.4, page 657) and 2-(2-chloroethoxy)tetrahydro-2H-pyran as described above.

$^1$H NMR (CDCl$_3$) d1.39 (6H s), 3.05 (1H broad), 3.95(4H s), 6.8 (1H d), 7.3 (2H m),

(16) 1-(2-Hydroxy-1-ethyl)-3,3,7-trimethyl-1,3-dihydro-2H-indol-2-one

Prepared from 3,3,7-trimethyl-1,3-dihydro-2H-indol-2-one (prepared by the method of Endler and Becker; Organic Syntheses Coll. vol. 4 page 657) and 2-(2-chloroethoxy) tetrahydro-2H-pyran as described above.

MS shows 220 (MH$^+$) base peak and 237 (M+NH$_4$)

(17) 3,3-Dimethyl-1-(2-hydroxy-1-ethyl)-5-methoxy-1,3-dihydro-2H-indol-2-one

Prepared from 3,3-dimethyl-5-methoxy-1,3-dihydro-2H-indol-2-one (prepared by the method of Endler and Becker; Organic Syntheses Coll. vol. 4 page 657) and 2-(2-chloroethoxy)tetrahydro-2H-pyran as described above.

$^1$H NMR (CDCl$_3$) d1.39 (6H s), 3.05 (1H broad), 3.82(3H s), 3.95(4H s), 6.8 (1H d), 7.3 (2H m), ( 18) 1-(2-Hydroxy-1-ethyl)-3,3,4-trimethyl-1,3-dihydro-2H-indol-2-one Prepared from 3,3,4-trimethyl-1,3-dihydro-2H-indol-2-one (prepared by the method of Endler and Becker; Organic Syntheses Coll. vol.4, page 657) and 2-(2-chloroethoxy)tetrahydro-2H-pyran as described above.

MS shows 220 (MH$^+$) base peak and 237 (M+NH$_4$)

(19) 1-(2-Hydroxy-1-ethyl)-3,3,6-trimethyl-1,3-dihydro-2H-indol-2-one

Prepared from 3,3,6-trimethyloxindole (prepared by the method of Endler and Becker; Organic Syntheses Coll. vol. 4 page 657) and 2-(2-chloroethoxy)tetrahydro-2H-pyran as described above.

MS shows 220 (MH$^+$) base peak and 237 (M+NH$_4$)

(20) 1-(2-Hydroxy-1-ethyl)-3-spiro-1'-cyclopropyl-1,3-dihydro-2H-indol-2-one

Prepared from 3-spiro-1'-cyclopropyl-1,3-dihydro-2H-indol-2-one and 2-(2-chloroethoxy)tetrahydro-2H-pyran.

$^1$H NMR (CDCl$_3$) d1.54 (2H m), 1.78 (2H m), 3.85 (4H m), 6.82 (1H d), 7.02 (2H m), 7.22 (1H m)

(21) 1-(2-Hydroxy-1-ethyl)-3-spiro-1'-cyclopentyl-1,3-dihydro-2H-indol-2-one

60% Sodium Hydride in oil dispersion (0.132 g, 3.29 mmols) was added to 3-spiro-1'-cyclopentyl-1,3-dihydro-2H-indol-2-one (0.513 g, 2.74 mmols) dissolved in N-methylpyrrolidinone (5 ml) followed by chloroethyl tetrahydropyran (0.541 g, 3.29 mmols) and the resultant mixture heated to 80C for 12 h. The mixture was cooled water (30 ml) was added and the product extracted into ethyl acetate (2×75 ml), dried (MgSO$_4$), filtered and concentrated in vacuo to give an oil. To this residue was added methanol (20 mls) and para-toluenesulfonic acid (0.08 g) and the mixture stirred at ambient temperature for 16 h. The solvent was evaporated in vacuo and the resulting oil was purified by column chromatography on silica with ethyl acetate/hexane to give an oil.

(22) 5-Fluoro-1-(2-hydroxy-1-ethyl)-1,3-dihydro-2H-indol-2-one

5-Fluoro-1,3-dihydro-2H-indol-2-one (2.4 g, 15.9 mmol) (prepared according to the method of Clark et al., Synthesis (1991) 871) was dissolved in freshly distilled tetrahydrofuran with tetramethylethylenediamine (3.7 g, 31.9 mmol) and was cooled to −75° C. under nitrogen. n-Butyllithium (2.4 equivalents) was added and the mixture was stirred at −75° C. for 40 minutes. Iodomethane (9 g, 63 mmol) was added and the mixture was allowed to warm to room temperature. After two hours' stirring at this temperature, water (5 ml) was added and the mixture was concentrated under reduced pressure, the resulting oil was taken up in dichloromethane, washed with dilute hydrochloric acid, dried (MgSO$_4$), filtered and concentrated to dry under reduced pressure to give a yellow oil. This oil was dissolved in N-methylpyrrolidone and stirred at room temperature under nitrogen. Sodium hydride (0.625 g, 15.6 mmol) was added and the mixture was stirred until gas evolution ceased. 2-(2-Chloroethoxy)tetrahydro-2H-pyran (2.5 g, 15 mmol) and sodium iodide (0.1 g, 0.66 mmol) was added and the mixture was warmed to 75° C. for 15 hours. Water was added and the mixture was concentrated under reduced pressure. The residue was taken up in ethyl acetate, washed (×3) with water, dried (MgSO$_4$), filtered and concentrated under reduced pressure. The resulting oil was taken up in methanol, para toluenesulphonic acid (0.1 g, 0.5 mmol) was added and the mixture was stirred at room temperature for 12 h. The mixture was concentrated under reduced pressure, taken up in ethyl acetate, washed (×3) with aqueous sodium hydrogen carbonate solution dried (MgSO$_4$), filtered and concentrated under reduced pressure. The resulting oil was purified by column chromatography on silica gel, (eluent hexane/ethyl acetate) to give 5-fluoro-1-(2-hydroxy-1-ethyl)-1,3-dihydro-2H-indol-2-one as a yellow oil. MS shows 224 (MH$^+$) base peak and 241 (M+NH$_4$)

(23) 5,6-Difluoro-3,3-dimethyl-1-(2-hydroxy-1-ethyl)-1,3-dihydro-2H-indol-2-one

Prepared from 5,6-difluoro-1,3-dihydro-2H-indol-2-one and converted to 5,6-difluoro-3,3-dimethyl-1-(2-hydroxy-1-ethyl)-1,3-dihydro-2H-indol-2-one as described for the synthesis of 3,3-dimethyl-5-fluoro-1-(2-hydroxy-1-ethyl)-1,3-dihydro-2H-indol-2-one.

$^1$H NMR (CDCl$_3$) d 1.38(6H s), 3.20(1H broad), 3.84(4H m), 6.7(1H dd), 7.03(1H dd)

(24) 1-(2-Chloroethyl)-1,3-dihydro-2H-indol-2-one 1-(2-Chloroethyl)-1H-indole-2,3-dione [C.A. Reg no. 77218-99-6] was suspended in acetic acid and hydrogenated at 60 p.s.i., at room temperature, in the presence of 70% perchloric acid and 5% palladium on charcoal for 24 h. The clear solution was filtered and concentrated under reduced pressure. The residue was purified by chromatography on silica gel, eluent chloroform, to give 1-(2-chloroethyl)-1,3-dihydro-2H-indol-2-one as a white solid, melting point 74° C.

(25) 1-(2-Chloro-1-ethyl)-5-fluoro-1H-indole-2,3-dione

5-Fluoro-1H-indole-2,3-dione was dissolved in dimethylformamide. Sodium hydride (60% dispersion in mineral oil)(1.2 equivalents) was added in portions with stirring and cooling (ice-water bath) and the mixture was stirred until gas evolution ceased. 1-Bromo-2-chloroethane (1.2 equivalents) was added dropwise. The mixture was stirred at room temperature for 24 hours and then quenched into water and extracted into chloroform. The combined organic phases were washed with water, dried (MgSO$_4$), filtered and concentrated under reduced pressure. The resulting oil was purified by chromatography on silica gel, eluent chloroform, to give 1-(2-chloro-1-ethyl)-5-fluoro-1H-indole-2,3-dione as a red solid.

Melting point 103° C.

(26) 1-(2-Chloro-1-ethyl)-1,3-dihydro-5-fluoro-2-oxo-2H-indole-3-spiro-2'-1,3 dithiane A solution of 1-(2-chloro-1-ethyl)-5-fluoro-1H-indole-2,3-dione, propanedithiol (1.2 equvalents) in chloroform was added dropwise to a stirred solution of boron trifluoride etherate in acetic acid and chloroform which was maintained at a gentle reflux throughout the addition. After 6 hours' reaction the mixture was cooled, washed with water and sodium hydrogen carbonate solution, dried (MgSO$_4$) and filtered through a pad of flash silica using chloroform as eluent. The combined fractions were evaporated under reduced pressure to give 1-(2-chloro-1-ethyl)-1,3-dihydro-5-fluoro-2-oxo-2H-indole-3-spiro-2'-1,3 dithiane.

Melting point 122° C.

(27) 1-(2-Chloro-1-ethyl)-5-fluoro-1,3-dihydro-2H-indole-2-one 1-(2-chloro-1-ethyl)-1,3-dihydro-5-fluoro-2-oxo-2H-indole-3-spiro-2'-1,3 dithiane was dissolved in a mixture of ethanol/tetrahydrofuran (3:2). Raney nickel was added and the mixture was heated under reflux with vigorous stirring for 3 h. The cooled solution was filtered, evaporated under reduced pressure and triturated with ether to give 1-(2-chloro-1-ethyl)-5-fluoro-1,3-dihydro-2H-indole-2-one as a white solid, melting point 127° C.

(28) 1-(2-Chloro-1-ethyl)-3,3-difluoro-1,3-dihydro-2H-indole-2-one 1-(2-Chloro-1-ethyl)-1H-indole-2,3-dione (1.1 g, 5.2 mmol) [C.A. Reg no. 77218-99-6] was heated to 65° C. under nitrogen in diethylaminosulfur trifluoride (3 ml). The reaction mixture was poured onto water and extracted with chloroform. The organic phase was washed with sodium hydrogen carbonate solution, dried (MgSO$_4$) and filtered to give 1-(2-chloro-1-ethyl)-3,3-difluoro-1,3-dihydro-2H-indole-2-one as a dark oil.

MS shows 231 and 233 (MH$^+$)

(29) 1-(2-Chloro-1-ethyl)-3,3,5-triifluoro-1,3-dihydro-2H-indole-2-one

Prepared from 1-(2-chloroethyl)-5-fluoro-1H-indole-2,3-dione and diethylaminosulfur trifluoride.

MS shows 249 and 251 (MH$^+$)

(30) 1-(2-Chloro-1-ethyl)-3-sriro-1'-cyclohexyl-1,3-dihydro-2H-indol-2-one

60% Sodium hydride in oil dispersion (0.46 g, 11.46 mmols) added was added to 3-spiro-1'-cyclohexyl-1,3-dihydro-2H-indol-2-one (1.922 g, 9.55 mmols) dissolved in dimethylformamide (25 mls) followed by bromochoroethane (1.643 g, 11.46 mmols) and the resultant mixture stirred for 2 hours at ambient temperature. Water (30 mls) was added and the product extracted into ethyl acetate (2×75 ml) the ethyl acetate layer dried ($MgSO_4$), filtered and concentrated in vacuo. The resulting oil purified by column chromatography on silica with ethyl acetate/hexane to give an oil).

(31) 3,3-Dimethyl-1-(2-methanesulfonyloxy-1-ethyl)-1,3-dihydro-2H-indol-2-one

Sodium hydride (60% oil dispersion, 2.98 g, 74.4 mmol) was washed with hexane, the hexane decanted and replaced with dimethylformamide (30 ml). To this mixture was added dropwise during 30 mins with stirring under nitrogen at ambient temperature 3,3-dimethyl-1,3-dihydro-2H-indol-2-one (10 g, 0.062 mol) in dimethylformamide (220 ml). This mixture was stirred for 1 h at ambient temperature then 2-(2-chloroethoxy)-2-tetrahydro-2H-pyran (12.25 g) was added in one portion, The mixture was heated to 80C for 1.25 h then poured into water (750 ml) and extracted with ethyl acetate (3×200 ml). The combined extracts were washed with water, dried ($MgSO_4$), filtered, and the filtrate evaporated in vacuo to give an oil 24.6 g, which was dissolved in methanol (50 ml) and treated with paratoluenesulfonic monohydrate (1.6 g, 8.4 mmol) and stirred for 16 h, at ambient temperature under nitrogen. The solvent was removed in vacuo and the residue dissolved in ethyl acetate and washed with aqueous potassium carbonate solution (2×), dried ($MgSO_4$), filtered, and evaporated in vacuo to give an oil 15.1 g which was dissolved in dichloromethane (75 ml) and triethylamine (9.41 g 93 mmol) was added followed by dropwise addition of methanesulfonyl chloride (6.0 ml, 77.5 mmol) during 4 mins and then stirred for 1.25 h. The solvent was then evaporated in vacuo and the residue partitioned between ethyl acetate and water, the organic extract washed with brine, dried ($MgSO_4$), filtered, and the filtrate evaporated in vacuo to give an oil 18.8 g. This oil was triturated with a small quantity of diethyl ether and the resultant cream coloured precipitate isolated by filtration and dried in vacuo to give a solid 13.16 g. Further purification was effected by trituration with warm diethyl ether to give a solid.

(32) 1-(2-Methanesulfonyloxy-1-ethyl)-3-spiro-1'-cyclopentyl-1,3-dihydro-2H-indol-2-one:

Triethylamine (0.246 g, 2.43 mmols) was added to 1-(2-hydroxy-1-ethyl)-3-spiro-1'-cyclopentyl-1,3-dihydro-2H-indol-2-one (0.433 g, 1.87 mmols) dissolved in dichloromethane (10 mls) followed by methanesulfonyl chloride (0.16 mls 2.06 mmols) and the mixture stirred at ambient temperature for 3 hours. Water was added (20 mls) the dichloromethane layer separated and dried ($MgSO_4$), filtered and concentrated in vacuo to give a solid.

(33) 1-Dimethylamino-2-(4-fluoro-2-nitro)phenylethene

A mixture of 4-fluoro-2-nitrotoluene (50 g, 0.32 mol), dimethylformamide dimethylacetal (76.77 g) and dimethylformamide (910 ml) were heated under relux under nitrogen with stirring for 7 h, cooled allowed to stand for 16 h, poured into ice-water (2000 ml), stirred for 15 mins, the resultant precipitate isolated by filtration, washed with water (500 ml), dried to give a red solid.

(34) 6-Fluoroindole

A 40 liter Cook hydrogenator was charged under a nitrogen atmosphere with 10% palladium on charcoal (9 g) suspended in toluene (400 ml). To this suspension was added 1-dimethylamino-2-(4-fluoro-2-nitro)phenylethene (137.2 g, 0.653 mol) in toluene (1400 ml) and the mixture hydrogenated at 80 psi for 3.5 h. The suspension was then filtered through a celite pad, which was washed through with toluene (2×200 ml) and the filtrate and washings evaporated under reduced pressure to give a brown oil which crystallised on standing to a yellow brown solid 93.65 g. This solid was dissolved in ethyl acetate-hexane (7:3) and filtered through a pad of flash silica. The required fractions were collected and evaporated under reduced pressure to give a pale brown solid.

Similarly prepared was 6-Cyanoindole.

(35) 7-Fluoroindole

2-Fluoronitrobenzene (20.0 g, 0.142 mols) dissolved in dry tetrahydrofuran (400 mls) and cooled to −50 deg C. Vinyl magnesium chloride (288 mls, 15% wt/vol) added at −45 deg C. and stirred at this temperature for one hour. Poured onto saturated ammonium chloride (600 mls) . Separated and aqueous extracted with diethyl ether (2×200 mls). Dried ($MgSO_4$), filtered and concentrated in vacuo to yield a dark oil which was purified column chromatography on silica using toluene as mobile phase. Fractions concentrated to yield a crystalline solid.

Similarly prepared was 6-Fluoro-7-methylindole.

(36) 7-Fluoroindole

To a stirred solution of boron trichloride in dichloromethane (1.0M, 3.6501, 3.65 mol) at −10C under nitrogen was added 2-fluoroaniline (387 g, 3.48 mol) and the temperature rose to 18C. The mixture was stirred for 45 mins before chloroacetonitrile (300 g, 3.97 mol) followed by aluminium chloride (500 g, 3.75 mol). 1,2-Dichloroethane (5.71) was added the mixture heated and the dichloromethane distilled from the reaction vessel. The dichloroethane solution was then heated at 78–80C for 18 h. The reaction mixture was then cooled to 2C and hydrochloric acid (2.5M 450 ml) was added slowly with a resultant exotherm. More hydrochloric acid (2.5M, 5.5501) was added and then the mixture was warmed to reflux for 10 mins then cooled. The dichloroethane layer was separated and the aqueous layer extracted with dichloromethane (11) combined with the dichloroethane, washed with brine (21), dried ($MgSO_4$), filtered and the solvent evaporated in vacuo to give a solid 321.7 g. This solid was dissolved in a mixture of dioxan (101) and water (11) and treated under nitrogen with sodium borohydride (73.0 g, 1.93 mol) then heated under reflux for 1 h. More sodium borohydride (12 g) was added and the mixture heated for a further 3 h, cooled to 45C and the solvent removed in vacuo. The residue was partitioned between dichloromethane (2000 ml) and water (2000 ml). The organic layer was separated, dried ($MgSO_4$), filtered and evaporated in vacuo to give an oil which was further purified by filtering through silica.

Similarly prepared was 6,7-Difluoroindole.

(37) 5,6-Difluoroindole

Fuming nitric acid (25 ml) was stirred with cooling (ice/water bath) and 3,4-difluorophenylacetonitrile (5 g, 32.7 mmol) was added dropwise. The mixture was left to stir for 15 h and was then poured onto ice. The mixture was neutralised with sodium hydrogen carbonate and extracted with dichloromethane. The combined organic phases were dried ($MgSO_4$), filtered and concentrated under reduced pressure to give 2(2'-nitro-4',5'-difluorophenyl)-acetonitrile as a yellow oil which was immediately in ethanol/acetic acid (19:1) and hydrogenated over 10% palladium on charcoal at 65 p.s.i. The reaction mixture was filtered and concentrated under reduced pressure. The oily residue was taken up in ethyl acetate and washed with aqueous sodium hydrogen carbonate solution. The combined organic phases were dried (MgSO$_4$), filtered and concentrated under reduced pressure to give 5,6-Difluoroindole as a yellow solid. Mass spectroscopy showed 154.1 (MH$^+$).

(38) 4-(6-Fluoroindol-3-yl)-1,2,5,6-tetrahydropyridine

Powdered potassium hydroxide (144.4 g) was added carefully to a mechanically stirred mixture of 6-fluoroindole (49.23 g, 0.364 mol) and piperidine monohydrate (111.93 g, 0.728 mol) in methanol (1500 ml) The mixture was then heated under reflux under nitrogen for 18 h and then more potassium hydroxide (40 g) was added and the reaction mixture heated under reflux for a further 4 h. The reaction mixture was allowed to cool to room temperature and poured onto ice-water (3000 ml) and stirred for 1 h and the precipitated solid isolated by filtration and dried at 50C in vacuo to give a solid.

(39) 4-(6-Fluoroindol-3-yl)piperidine

A mixture of platinum oxide (1.0 g) in ethanol (37.5 ml) and glacial acetic acid (12.5 ml) was treated under nitrogen with 4-(6-fluoroindol-3-yl)-1,2,5,6-tetrahydropyridine (20 g, 92.6 mmol) in ethanol (187.5 ml) and glacial acetic acid (62.5 ml). The nitrogen was evacuated and hydrogen was admitted. The reaction mixture was then hydrogenated at 60 psi until the reaction was complete by tlc. The catalyst was removed by filtration and the solvent evaporated in vacuo to give a yellow solid which after drying at 60C in vacuo weighed.

EXAMPLE 1

3,3-Dimethyl-1-{2-[4-(7-fluoroindol-3-yl)-1,2,5,6-tetrahydro-1-pyridyl]-1-ethyl}-1,3-dihydro-2H-indol-2-one 4-(7-Fluoroindol-3-yl)-1,2,5,6-tetrahydropyridine (2.0 g, 9.26 mmols), 3,3-dimethyl-1-(2-methanesulfonyloxy-1-ethyl)-1,3-dihydro-2H-indol-2-one (2.623 g, 9.26 mmols), sodium carbonate (2.947 g,27.8 mmols),water (20 mls) combined and heated to 90 deg C. for 3 hours. Extracted into ethyl acetate (2×50 ml). Dried (MgSO$_4$),filtered and concentrated in vacuo. The resultant solid was recrystallised from ethyl acetate and then converted to the hydrochloride salt (0.85 g).m.p 235–236 deg. C.

EXAMPLE 2

3,3-Dimethyl-1-{2-[4-(6-fluoro-7-methylindol-3-yl)-1,2,5,6-tetrahydro-1-pyridyl]-1-ethyl}-1,3-dihydro-2H-indol-2-one hydrochloride 3,3-dimethyl-1-(2-methanesulfonyloxy-1-ethyl)-1,3-dihydro-2H-indol-2-one (6.21 g, 0.0219 mols) and 4-(6-fluoro-7-methylindol-3-yl)-1,2,5,6-tetrahydropyridine (5.05 g, 0.0219 mols) were dissolved in dry acetonitrile (220 mL). To this potassium carbonate (3.5 g, 0.026 mol) and potassium iodide (4.23 g, 0.026 mol) were added. The mixture was stirred, whilst heating under reflux, for 4 h. The hot mixture was filtered off from inorganic material after this time and the filtrate was evaporated to dryness in vacuo. The residue was dissolved in choroform, to which a minimum of methanol was added to aid solubility and filtered off from any remaining inorganic materials. This filtrate was column chromatographed using initially chloroform with "flash" silica gel as the stationary phase. The bulk of the material was eluted using 2% methanol in chloroform, any remaining material was removed with 5% methanol in chloroform.

The fractions containing product were bulked and evaporated to dryness, in vacuo, the residue was triturated with ethyl acetate, filtered off and dried in a vacuum oven at 60° C. The weight of freebase=6.81 g, melting point=219° C.

This material (1 g) was dissolved in boiling ethyl acetate (100 mL) and enough ethanolic hydogen chloride was added to this solution to render it acid when tested with pH paper. The solution was chilled and a hydrochloride salt crystallised out. The salt was filtered off, washed with ethyl acetate, ether, and dried, melting point=228.8–233.3° C.

EXAMPLE 3

3,3-Dimethyl-1-{2-[4-(7-fluoroindol-3-yl)-1-piperidinyl]-1-ethyl)-1,3-dihydro-2H-indol-2-one Monohydrochloride 3,3-Dimethyl-1-{2-[4-(7-fluoroindol-3-yl)-1,2,5,6-tetrahydro-1-pyridyl]-1-ethyl}-1,3-dihydro-2H-indol-2-one (0.6 g, 1.36 mmol) dissolved in ethanol (40 mls) and acetic acid (4 mls) was added to 10% platinum oxide/charcoal. Hydrogen was admitted for 12 h at 60 psi the catalyst was then removed by filtration, the catalyst washed with ethanol (3×75 mls), concentrated in vacuo and the resulting oil purified by column chromatography on silica with ethyl acetate/Hexane. The fractions containing product were collected and the solvent evaporated in vacuo to give a solid which was converted to the hydrochloride, which was subsequently dried in vacuo to give a solid, mp 172–174° C.

EXAMPLE 4

3,3-Dimethyl-1-{2-[4-(6-fluoroindol-3-yl)-1-piperidinyl]-1-ethyl}-1,3-dihydro-2H-indol-2-thione Monohydrochloride Phosphorus pentasulfide (0.164 g) was added to 3,3-dimethyl-1-(2-[4-(6-fluoroindol-3-yl)-1-piperidinyl]-1-ethyl}-1,3-dihydro-2H-indol-2-one (0.5 g, 1.23 mmol) dissolved in pyridine (15 mls) and the mixture heated under reflux for 12 hours. The resultant mixture concentrated in vacuo and dissolved in ethyl acetate (50 mls) and washed with water (50 ml). The ethyl acetate layer dried (MgSO$_4$), filtered and concentrated in vacuo to give a solid which was purified by column chromatography using silica/dichloromethane then ethyl acetate. The fractions containing product were concentrated and converted to the hydrochloride salt, mp 227–229C.

Similarly prepared were:

3,3-Dimethyl-N,N-dimethyl-1-{2-[4-(6-fluoroindol-3-yl)-1,2,5,6-tetrahydro-1-pyridyl]-1-ethyl}-1,3-dihydro-2H-2-oxo-indole-5-carboxamide hydrochloride. mp=210.2–215° C.

1-{2-[4-(6-Chloroindol-3-yl)-1,2,5,6-tetrahydro-1-pyridyl]-1-ethyl}-3,3-dimethyl-N,N-dimethyl-1,3-dihydro-2H-2-oxo-indole-5-carboxamide. mp=225° C.

3,3-Dimethyl-1-{2-[4-(7-chloroindol-3-yl)-1,2,5,6-tetrahydro-1-pyridyl]-1-ethyl}-1,3-dihydro-2H-indol-2-one hydrochloride. mp=248.9–249.9° C.

3,3-Dimethyl-1-{2-[4-(6-fluoro-7-methylindol-3-yl)-1,2,5,6-tetrahydro-1-pyridyl]-1-ethyl}-1,3-dihydro-2H-indol-2-one hydrochloride. mp=228.8–233.3° C.

1-{-2-[4-(6,7-Difluoroindol-3-yl)-1,2,5,6-tetrahydro-1-pyridyl]-1-ethyl}-3,3-dimethyl-5-fluoro-1,3-dihydro-2H-indol-2-one hydrochloride. mp >250° C.

3,3-Dimethyl-5,6-difluoro-1-{2-[4-(6-fluoroindol-3-yl)-1,2,5,6-tetrahydro-1-pyridyl]-1-ethyl}-1,3-dihydro-2H-indol-2-one hydrochloride. mp=227–229° C.

1-{2-[4-(6-Fluoroindol-3-yl)-1,2,5,6-tetrahydro-1-pyridyl]-1-ethyl}-3-methyl-3-methylthio-1,3-dihydro-2H-indol-2-one hydrochloride. mp=165–168° C.

1-{2-[4-(6-Fluoroindol-3-yl)-1-piperidinyl]-1-ethyl}-3,3,5-trimethyl-1,3-dihydro-2H-indol-2-one hydrochloride. mp=220–222° C.

5,6-Difluoro-3,3-dimethyl-1-{2-[4-(6-fluoroindol-3-yl)-1-piperidinyl]-1-ethyl}-1,3-dihydro-2H-indol-2-one hydrochloride. mp=231–233° C.

3,3-Dimethyl-1-{2-[4-(6-fluoro-1-methylindol-3-yl)-1-piperidinyl]-1-ethyl}-5-methoxy-1,3-dihydro-2H-indol-2-one hydrochloride. mp=252–255° C.

3-Ethyl-1-{2-[4-(6-fluoroindol-3-yl)-1-piperidinyl]-1-ethyl}-3-methyl-1,3-dihydro-2H-indol-2-one hydrochloride. mp=221–223° C.

3,3-Dimethyl-5-fluoro-1{2-[4-(6-fluoro-1-methylindol-3-yl)-1-piperidinyl]-1-ethyl}-1,3-dihydro-2H-indol-2-one hydrochloride. mp >260° C.

1-{2-[4-(5,6-Difluoroindol-3-yl)-1-piperidinyl]-1-ethyl}-3,3-dimethyl-1,3-dihydro-2H-indol-2-one hydrochloride. mp>260° C.

3-Ethyl-1-{2-[4-(6-fluoroindol-3-yl)-1,2,5,6-tetrahydro-1-pyridyl]-1-ethyl}-3-methyl-1,3-dihydro-2H-indol-2-one hydrochloride. mp=196–204° C.

1-{2-[4-(6-Fluoroindol-3-yl)-1,2,5,6-tetrahydro-1-pyridyl]-1-ethyl}-3,3,5-trimethyl-1,3-dihydro-2H-indol-2-one hydrochloride. mp=206–222° C.

3,3-Dimethyl-5-fluoro-1-{2-[4-(7-fluoroindol-3-yl)-1-piperidinyl]-1-ethyl}-1,3-dihydro-2H-indol-2-one hydrochloride. mp=198–200° C.

5-Chloro-3,3-dimethyl-1-{2-[4-(6-fluoroindol-3-yl)-1,2,5,6-tetrahydro-1-pyridyl]-1-ethyl}-1,3-dihydro-2H-indol-2-one hydrochloride. mp=233.9–236.2° C.

1-{2-[4-(6,7-Dichloroindol-3-yl)-1,2,5,6-tetrahydro-1-pyridyl]-1-ethyl}-3,3-dimethyl-1,3-dihydro-2H-indol-2-one hydrochloride. mp=262–266° C.

1-{2-[4-(5,7-Difluoroindol-3-yl)-1,2,5,6-tetrahydro-1-pyridyl]-1-ethyl}-1,3-dihydro-3-spiro-4'-(1'-methylpiperidino)-2H-indol-2-one. mp 210–212° C.

3,3-Dimethyl-1-{2-[4-(5-fluoroindol-3-yl)-1,2,5,6-tetrahydro-1-pyridyl]-1-ethyl}-1,3-dihydro-2H-indol-2-one hydrochloride. mp 230° C.

3,3-Dimethyl-1-{2-[4-(4-fluoroindol-3-yl)-1,2,5,6-tetrahydro-1-pyridyl]-1-ethyl}-1,3-dihydro-2H-indol-2-one hydrochloride. mp=235.6–236.6° C.

3,3-Dimethyl-1-{2-[4-(5-fluoro-1-methylindol-3-yl)-1,2,5,6-tetrahydro-1-pyridyl]-1-ethyl}-1,3-dihydro-2H-indol-2-one hydrochloride. mp=194–197° C.

We claim:
1. A compound of the formula:

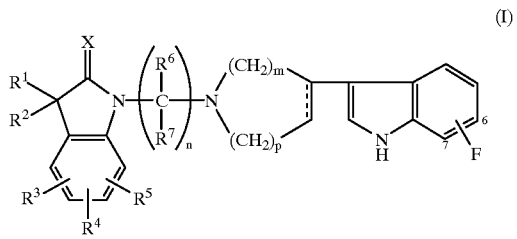

in which n is 1 to 6, m is 1 or 2 and p is 1 or 2, $R^1$ and $R^2$ are each hydrogen, $C_{1-4}$ alkyl, $C_{1-4}$ alkoxy, HO—$C_{1-4}$ alkyl, $C_{1-4}$ alkoxy-$C_{1-4}$ alkyl, $C_{1-4}$ alkylthio, halo, optionally substituted phenyl, optionally substituted phenyl-$C_{1-4}$ alkyl, or $R^1$ and $R^2$ together with the carbon atom to which they are attached form a $C_{3-6}$ cycloalkyl group, >C═O, C═NOR' where R' is hydrogen or $C_{1-4}$ alkyl, $R^3$, $R^4$ and $R^5$ are each hydrogen, halo, nitro, $C_{1-4}$ alkyl, $C_{1-4}$ alkoxy, $C_{1-4}$ alkyl-CO—, where m is 0, 1 or 2, R'R"N—$SO_2$—, —COOR', —CONR'R", —NR'R", —N(OR')COOR", —COR', —$NHSO_2R'$, where R' and R" are each hydrogen or $C_{1-4}$ alkyl, $R^6$ and $R^7$ are each hydrogen or $C_{1-4}$ alkyl, X is oxygen or sulphur, the dotted line represents an optional double bond, and the fluorine atom is attached at the 6- or 7-position;

and salts thereof.

2. A compound according to claim 1 in which the fluorine substituent is in the 6-position, and X is oxygen.

3. A compound according to claim 2 in which the dotted line represents a double bond.

4. A compound according to claim 3 in which r is 2, m is 2 and p is 1.

5. A compound according to claim 4 in which $R^1$ and $R^2$ are each hydrogen, $C_{1-4}$ alkyl or $C_{1-4}$ alkylthio, and $R^6$ and $R^7$ are hydrogen.

6. A compound according to claim 4 in which $R^1$ and $R^2$ are both $C_{1-4}$ alkyl or benzyl.

7. A pharmaceutical formulation comprising a compound according to any of claims 1 to 6 associated with a pharmaceutically acceptable diluent or carrier therefor.

8. A method of treating a disorder of the central nervous system which comprises administering an effective amount of a compound according to claim 1, or a pharmaceutically acceptable salt thereof.

* * * * *